United States Patent
Gladden

(10) Patent No.: US 11,894,116 B1
(45) Date of Patent: Feb. 6, 2024

(54) APPARATUS FOR EXTENDING LONGEVITY AND A METHOD FOR ITS USE

(71) Applicant: Oceandrive Ventures, LLC, Rio Grande, PR (US)

(72) Inventor: Jeffrey Gladden, Rio Grande, PR (US)

(73) Assignee: Oceandrive Ventures, LLC

( * ) Notice: Subject to any disclaimer, the term of this patent is extended or adjusted under 35 U.S.C. 154(b) by 0 days.

(21) Appl. No.: 18/072,987

(22) Filed: Dec. 1, 2022

(51) Int. Cl.
  G16H 20/00 (2018.01)
(52) U.S. Cl.
  CPC .................................. G16H 20/00 (2018.01)
(58) Field of Classification Search
  CPC ....................................................... G16H 20/00
  USPC ............................................................ 705/2
  See application file for complete search history.

(56) References Cited

U.S. PATENT DOCUMENTS

| | | | |
|---|---|---|---|
| 6,269,339 B1 | 7/2001 | Silver | |
| 2007/0118398 A1 | 5/2007 | Perls | |
| 2008/0220092 A1* | 9/2008 | Dipierro | A61P 3/00 514/249 |
| 2012/0221350 A1* | 8/2012 | Kenedy | G06F 16/24575 705/2 |
| 2017/0290516 A1* | 10/2017 | Nguyen | G16H 50/30 |
| 2020/0380887 A1 | 12/2020 | Mason | |
| 2022/0076834 A1 | 3/2022 | Hanlon | |

FOREIGN PATENT DOCUMENTS

| | | | | |
|---|---|---|---|---|
| ES | 2715102 T3 * | 5/2019 | ......... | A61B 5/02007 |
| WO | WO-2016019149 A1 * | 2/2016 | ........... | C12Q 1/6883 |
| WO | WO-2016094330 A2 * | 6/2016 | ....... | G01N 33/57423 |

OTHER PUBLICATIONS

Caswell, Ha; Healthy longevity from incidence-based models: More kinds of health than stars in the sky; Demographic Research 45: 397-452,397A-397B. Max Planck Institut für Demografische Forschung. (Jul.-Dec. 2021) (Year: 2021).*

* cited by examiner

Primary Examiner — Hiep V Nguyen
(74) Attorney, Agent, or Firm — Caldwell Intellectual Property Law

(57) ABSTRACT

An apparatus for extending longevity, wherein the apparatus includes at least a processor and a memory communicatively connected to the at least a processor. The memory containing instructions configuring at least a processor to receive a longevity measurement pertaining to a user. The memory containing instructions further configuring the processor to select a target longevity factor as a function of the longevity measurement and then identify a longevity treatment plan as a function of the target longevity factor. The memory containing instructions further configuring the processor to generate a longevity treatment protocol as a function of the longevity treatment and the longevity measurement.

18 Claims, 7 Drawing Sheets

APPARATUS FOR EXTENDING LONGEVITY AND A METHOD FOR ITS USE

FIELD OF THE INVENTION

The present invention generally relates to the field of medical treatments. In particular, the present invention is directed to an apparatus for extending longevity and a method for its use.

BACKGROUND

Extending human longevity is a complex, multifaceted problem. Depending on health status, issues, and goal of patients, a personalized treatment may be necessary to help patients improve their overall health, and thus live longer. Existing solutions to this problem are not satisfactory.

SUMMARY OF THE DISCLOSURE

In an aspect, an apparatus for extending longevity, wherein the apparatus includes at least a processor and a memory communicatively connected to the at least a processor. The memory containing instructions configuring at least a processor to receive a longevity measurement pertaining to a user. The memory containing instructions further configuring the processor to select a target longevity factor as a function of the longevity measurement and then identify a longevity treatment plan as a function of the target longevity factor. The memory containing instructions further configuring the processor to generate a longevity treatment protocol as a function of the longevity treatment and the longevity measurement.

In another aspect, a method for extending longevity is shown, the method includes receiving, using a processor, a longevity measurement pertaining to a user. The processor selects a target longevity factor as a function of the longevity measurement. Additionally, the processor identifies a longevity treatment plan as a function of the longevity measurement. A longevity treatment protocol is generated as a function of the longevity treatment and the longevity measurement.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for extending longevity. An apparatus may comprises at least a processor and a memory communicatively connected to the at least a processor. The processor may further be configured to receive a longevity measurement pertaining to a user. The processor then may select a target longevity factor as a function of the longevity measurement. A longevity treatment is then identified as a function of the target longevity factor. The processor then may generate a longevity treatment protocol pertaining to the user as a function of the longevity treatment and the longevity measurement.

In an embodiments, methods and systems described herein may involve one or more aspects of longevity. As used in this disclosure, "longevity" is the time that elapses between the birth and death of the user. In some embodiments, longevity may include a statical measurement in unit of years; for instance, without limitation, longevity may include age of the user. In some embodiments, longevity may include a life expectancy, wherein the life expectancy is a statical measure of the average time the user is expected to live, based on demographic factors such as, without limitation, time of birth, current age, gender, and the like thereof. In another embodiments, methods and systems described herein may involve one or more aspects of extending the longevity. In some embodiments, extending longevity may include an age reversal. As used in this disclosure, an "age reversal" is a process that reduces or attempts to reduce a user's aging process. In a non-limiting example, age reversal may include rejuvenation. In some embodiments, age reversal may include one or more process of repairing one or more damages that are associated with aging; for instance, without limitation, age reversal may include replacement of damaged tissue with new tissue for the user. In another non-limiting example, age reversal may include implantation of stem cells into a tissue scaffold that guides restoration of the user. As a further non-limiting example, age reversal may include addition of actual or projected years or other units of time to life expectancy, longevity, or the like.

Figure 1:
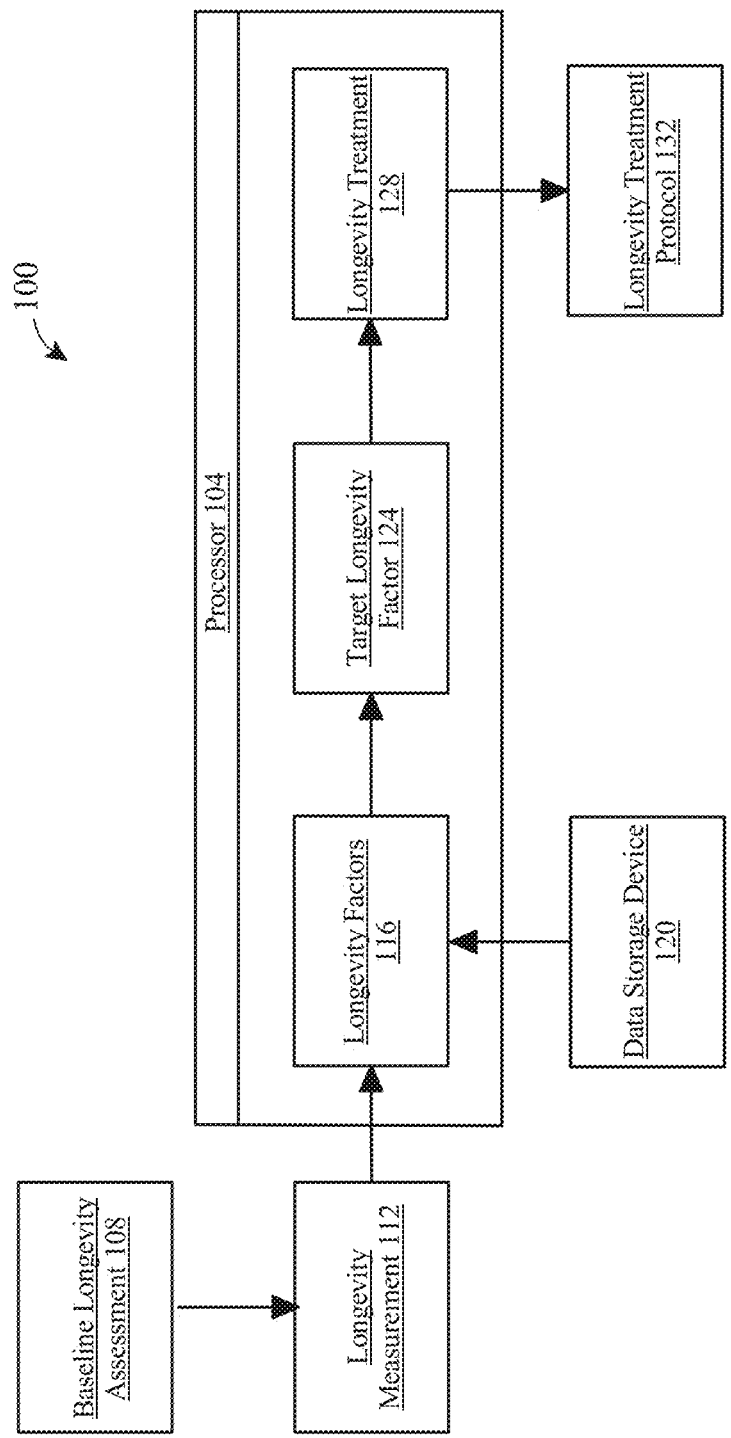
FIG. 1 is a block diagram of an exemplary embodiment of an apparatus for extending longevity.

Referring now to FIG. 1, an exemplary embodiment of an apparatus 100 for extending longevity is illustrated. System includes a processor 104. processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of system 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, processor 104 may receive, pertaining to a user, a longevity measurement 112. As used in this disclosure, "receive" from a user means accepting, collecting, or otherwise receiving input from a user and/or device. A "longevity measurement", as used in this disclosure, is data that relates to the user's system or performance metrics. As used in the current disclosure, "systems" are biological systems within a human body. In some cases, user's systems may include, but is not limited to, circulatory, nervous, skeletal, respiratory, reproductive, endocrine, integumentary, renal, digestive, and muscular systems. Each organ may have one or more specialized role in the body and is made up of distinct tissues. Additionally, user's systems may include heart, lungs, kidneys, or any other organ system. This may also include the components of a given system. In a non-limiting example, lungs may be component of respiratory system. "Performance metrics," as used in this disclosure, are numeric or linguistic measurement of the evaluation of the ability to perform one or more predetermined tasks. Predetermined tasks may include, but are not limited to, walking, running, squatting, jumping, lifting, sleeping, eating, thinking, learning, and the like. As used in this disclosure, an "user" is an individual who uses apparatus 100. For example, user may be a patient. As another example, user may be a doctor. In an embodiment, longevity measurement 112 may include information collected from a standard health screening. In some cases, a standard health screening may include, but is not limited to, tests like blood test, hearing test, vision test, height, weight, and body mass index (BMI), and the like. In other embodiment, longevity measurement 112 may include medical history, diet, exercise, sleep, time, and geographical location data of the user. In an embodiment, longevity measurement 112 may be stored in a data storage device 120, such as a longevity database 300 disclosed with reference to FIG. 3.

With continued reference to FIG. 1, Longevity measurement 112 may include one or more measurable longevity markers. As used in this disclosure, a "longevity marker" is a biomarker that indicates one or more aspects of the longevity of the user. As used in the current disclosure, a "biomarker" is a biological molecule found in blood, other body fluids, or tissues that is a sign of a normal or abnormal process, or of a condition or disease. In an embodiment, biomarker may be used to see how well the body responds to a treatment for a disease or condition. In some cases, measurable biomarker may include, but is not limited to, yH2A.X immunohistochemistry, Leukocyte telomere length, MIR31HG, p16INK4a, Senescence-associated secretory phenotype (SASP) proteins, Measures of DNA methylation, SIRT1, SIRT2, SIRT3, SIRT6, SIRT7, Dosage of circulating microRNAs (miR-34a, MiR-21, miR-126-3p, miR-151a-3p, miR-181a-5p, miR-1248), P31 MRI spectroscopy, growth differentiating factor 15 (GDF15), Target of rapamycin (TOR), Protein carbonylation, Advanced glycation end products, Insulin-like growth factor (IGF-1), HGBA1c, IL-6, TNF-α, CRP (C-reactive protein), and TNFRII (tumor necrosis factor-α RII). In some embodiments, biomarkers may be measured using various pathways including, but is not limited to, DNA repair mechanisms, DNA modifications, telomere length, markers of DNA damage response, telomerase activity, senescent markers in blood and tissue, DNA methylation, histone acetylation, noncoding RNA, autophagy markers, chaperon proteins, proliferative capacity in vitro, growth hormone axis, and metabolism alterations. In an embodiment, longevity measurements 112 may include, but it is not limited to, mTOR/AMPK, senescent cell cytokine burden, proteostasis, autophagy, thymus gland status, mitochondrial regeneration of target tissues, hypothalamic stem cell status, insulin/glucose status, AMPK activation status, mitochondrial UPR and FOXO signaling, DNA methylation rate, redox balance, glycation, oncogenic potential, genetic predisposition for aging, thyroid panel, glycation age, and the like.

With continued reference to FIG. 1, receiving longevity measurement 112 may further include selecting a baseline longevity assessment 108 for the user and receiving longevity measurement 112 pertaining to the user as a function of the baseline longevity assessment 108. As used in this disclosure, a "baseline longevity assessment" is a set of questions answered by patients. This may include, but is not limited to, questions about personal behaviors, risks, life-changing events, health goals and priorities, and overall physical and/or mental health of the user. In some cases, baseline longevity assessment 108 may also be a set of actions, performed by patients, that may include, but is not limited to, walking, running, squatting, jumping, lifting, sleeping, eating, thinking, learning, and the like. In an embodiment, selecting baseline longevity assessment 108 may further include an initial baseline longevity assessment and periodic repetition of baseline longevity assessment 108. In some cases, periodic repetition may include, but is not limited to, hourly, daily, biweekly, weekly, bimonthly, monthly, yearly, and the like. In another embodiment, baseline longevity assessment 108 may include an assessment modification on the baseline longevity assessment 108 based on one or more post longevity measurement of the user. As used in this disclosure, a "post longevity measurement" is a subsequent longevity measurement pertaining to a user. In some cases, post longevity measurement may include a measurement timestamp, wherein the measurement timestamp may include date and time post longevity measurement pertain to user have been measurement and/or recorded. In a non-limiting example, a user may take a first longevity assessment for a first longevity measurement at a first measurement timestamp and the second longevity assessment for a second longevity measurement at a second measurement timestamp, wherein the second measurement timestamp may be greater than the first measurement timestamp, and wherein the second longevity measurement may be therefore a post longevity measurement of the user. First longevity assessment may be modified based on second longevity measurement and produce a second longevity assessment, wherein the second longevity assessment may be longevity assessment user take for further longevity measurements. Additionally, post longevity measurement may be stored and/or gathered from a data storage device 120, such as longevity database 300 disclosed with reference to FIG. 3.

With continued reference to FIG. 1, processor 104 may be configured to select a target longevity factor 124 as a function of the longevity measurement. In some embodiments, target longevity factor 124 may be selected from a plurality of longevity factors 116. As used in this disclosure, a "longevity factor" is an aspect that affects the length and/or the quality of the life span of the user. In some cases, longevity factor 116 may include, but is not limited to, cancer risk, musculoskeletal healing, organ healing, gut healing, brain health, peripheral neuropathy, long haul covid, heart health, lung health, kidney health, liver health, pancreatic health, cosmetics, altered cell communication, genomic instability, telomere attrition, epigenetic alterations, loss of proteostasis, deregulated nutrient-sensing, mitochondrial dysfunction, cellular senescence, stem cell exhaustion, and the like. In some cases, longevity factor 116 may be calculated as a function of one or more longevity measurements 112. In an embodiment, longevity factor 116 may be stored in data storage device 120, such as longevity database 300 disclosed with reference to FIG. 3. Additionally, in some embodiments, longevity factor 116 may contain an evaluation score including a range of numbers or grades. In an embodiment, evaluation score may be used to determine the degree of wellness of the given longevity factor 116. In a non-limited example, an evaluation score of the cancer risk longevity factor may be scored from 0 to 100. Evaluation score of the cancer risk longevity factor that is close to 0 means the risk of developing cancer is low. Evaluation score of the cancer risk longevity factor that is close to 100 means the risk of developing cancer is high. Additionally, the risk of developing cancer for a user with a cancer risk longevity factor evaluation score of 50 is lower than a user with cancer risk longevity factor evaluation score of 80. A "target longevity factor", as described herein, is the most important longevity factor of the user to be improved and/or balanced. In an embodiment, target longevity factor 124 may identify a disbalanced health area of the user. As used in this disclosure, a "disbalanced health area" is a longevity factor associated with low or high evaluation score based on the longevity factor and the scale of the evaluation metric for that longevity factor. In an embodiment, disbalanced health area of the user may be an aspect where user lack essential elements or/and need to be improved. In another embodiment, disbalanced health area may be an unhealthy system of the user. For example, a longevity factor x of the user within all the longevity factors LFs, with evaluation score that is discovered to be the minimum (MIN) or maximum (MAX) evaluation score within all the longevity factors LFs, is considered as a disbalance health area.

$$LFx \in LFs : x = MIN(LFs) | MAX(LFs)$$

Processor 104 may select target longevity factor 124 using a machine-learning process trained with longevity factor training data. Longevity factor training data is a plurality of data entries containing a plurality of inputs that are correlated to a plurality of outputs for training a processor by a machine-learning process to align, classify, and determine the target longevity factor of the user. In an embodiment, the inputs of the longevity factor training data may contain one or more longevity measurements 112 and the outputs of the longevity factor training data may contain target longevity factors. In some cases, longevity factor training data may be obtained from a data storage device 120. In a non-limiting example, data storage device 120 may be a longevity database 300. Longevity database 300 is described in further detail with reference to FIG. 3. In some embodiments, longevity factor training data may include manually labeled data. As a non-limiting example, Longevity factor 116 and/or longevity measurements 112 may be manually collected and labeled by the user and/or a medical professional. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, processor 104 may be configured to identify a longevity treatment 128 as a function of the target longevity factor. As used in this disclosure, a "longevity treatment" is detailed instructions or a prescription. In some embodiments longevity treatment 128 may include but is not limited to remediation of a physical or mental health problem or/and shortened life span. In other embodiments, longevity treatment 128 may include, without limitation, one or more strategies for age reversal. In an embodiment, longevity treatment 128 may be stored in a data storage device, such as the longevity database 300 disclosed with reference to FIG. 3. In an embodiment, longevity treatment 128 may include one or more consumable longevity-extending ingredients. As used in this disclosure, a "consumable longevity-extending ingredient" is a particular ingredient that has an effect on longevity and that can be digested by user. In some cases, consumable longevity-extending ingredient may include, but is not limited to, vitamin D, Zinc, spermidine, hydroxyl berberine, rapamycin, metformin, pterostilbene, carnosine, curcumin, thyroid extract, and the like. In another embodiment, longevity treatment 128 may include, but is not limited to executable longevity-extending procedures such as plasmapheresis, VSELS therapy, ozone therapy and the like. Additionally, longevity treatment 128 may include a lifestyle factor. As described in this disclosure, a "lifestyle factor" is a factor in user's daily life that may affect the user's the risk of injury or disease or the length of the life span of the user. In some cases, life factor may include, but is not limited to, exercising regularly, maintaining a healthy body weight, avoiding stationary sitting, avoiding sugar, eating more vegetables and fruits, drinking more water, going to bed early, quitting smoking and the like.

With continued reference to FIG. 1, processor 104 may be configured to generate, pertaining to the user, a longevity treatment protocol 132 as a function of the longevity treatment 128 and the longevity measurement 112 of the user. As used in this disclosure, a "longevity treatment protocol" is a detailed plan of a scientific or medical experiment, treatment, or procedure aimed at extending the longevity of the user. In some cases, longevity treatment protocol may include an implementation of the age reversal. In an embodiment, longevity treatment protocol 132 may include, but is not limited to, one or more longevity treatments 128 corresponding to one or more longevity factors 116. In a non-limited example, a longevity treatment protocol for reducing cancer risk may include longevity treatment 128, wherein longevity treatment 128 may include, but is not limited to, a healthy diet plan, vaccination, exercise plan, drink limitation and the like correspond to the longevity factor of cancer risk. In an embodiment, the longevity treatment protocol 132 may be stored in a data storage device 120, such as longevity database 300 disclosed with reference to FIG. 3. In an embodiment, generating longevity treatment protocol 132 may include updating longevity treatment protocol as a function of one or more post longevity measurement in addition to longevity measurement pertaining to user and a trained machine-learning processes described further below in this disclosure. Longevity treatment protocol may be updated at any given time interval such as, without limitation, hourly, daily, weekly, bi-weekly, monthly, and the like thereof. Process of updating longevity treatment protocol and/or any other processing steps described in this disclosure may be performed at any given time interval. For instance, trained machine-learning process may take in one or more post longevity measurements in addition to, optionally, longevity measurement 112 pertaining to user from a data storage device 120 such as a longevity database 300 as input and output an updated longevity treatment protocol 132. In some embodiments, trained machine learning process may also take longevity treatment protocol as input. In some cases, updating may include, but is not limited to, modifying instructions in longevity treatment 128, adding/removing longevity treatment 128, adding/removing longevity factor 116, switching target longevity factor 124 and the like thereof. In some embodiments, an updated machine-learning process may be used to generate an updated longevity treatment protocol. In some embodiments, update machine-learning process may be trained using update training data, where in update training data may include inputs comprising longevity treatment protocol 132, one or more post-longevity measurements and/or longevity measurement 112 correlated to outputs comprising an updated longevity measurement protocol. In some embodiments, update machine-learning process may take longevity treatment protocol 132, one or more post-longevity measurements and, optionally, longevity measurement 112 as input and output an updated longevity measurement protocol. In some embodiments, updated longevity treatment protocol may be generated using user feedback. User feedback may include qualitative or quantitative evaluations of longevity treatment protocol. Quantitative evaluations may include a rating, such as a rating out of 10, 5, 100, and the like. Qualitative evaluations may include a "good," "bad," a user's satisfaction, a user's comfort level, and the like. In some embodiments, trained machine learning process and/or update machine learning process may take as input, user feedback. In some embodiments, trained machine learning process and/or update machine learning process may be trained using training data including examples of user feedback as inputs. User feedback may be inputted by the user using any suitable means including, but not limited to, selecting an option on a screen, entering text, verbal communication, selecting a rating on a screen, clicking a button, and the like. In another embodiment, generating the longevity treatment protocol 132 may include selecting longevity treatment protocol 132 from the data storage device 120 with similar longevity measurements 112 and/or target longevity factors 124, such as the longevity database 300. Longevity database 300 disclosed here will be described in further detail below.

Processor 104 may generate longevity treatment protocol 132 using a machine-learning processes trained with longevity treatment training data. Longevity treatment training data is a plurality of data entries containing a plurality of inputs that are correlated to a plurality of outputs for training a processor by a machine-learning process to align, classify, and determine the target longevity factor to/of the user. In an embodiment, the inputs of the longevity treatment training data may contain one or more longevity treatments 128 and corresponding longevity measurement 112, and the outputs of the longevity treatment training data may contain longevity treatment protocols 132. In some cases, longevity treatment training data may be obtained from data storage device 120. In a non-limiting example, data storage device 120 may be longevity database 300. Longevity database 300 is described in further detail with reference to FIG. 3. In some embodiments, longevity treatment training data may include manually labeled data. As a non-limiting example, longevity treatment 128 and corresponding longevity measurement 112, and/or longevity treatment protocol 132 may be manually collected and labeled by the user and/or a medical professional. As a non-limiting example, a medical professional may receive examples of longevity factors 116 and target longevity factors 124 and be asked to prescribe a longevity treatment 128; this dataset may then be used as longevity treatment training data. In some embodiments, longevity treatment training data may be derived from examples including a plurality of longevity treatment protocols 132. As a non-limiting example, longevity treatment training data may be chosen from real-life examples of longevity treatments 128 or longevity treatment protocols 132 for patients and the associated longevity factors 116 and/or target longevity factors 124 of those patients. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Figure 2:
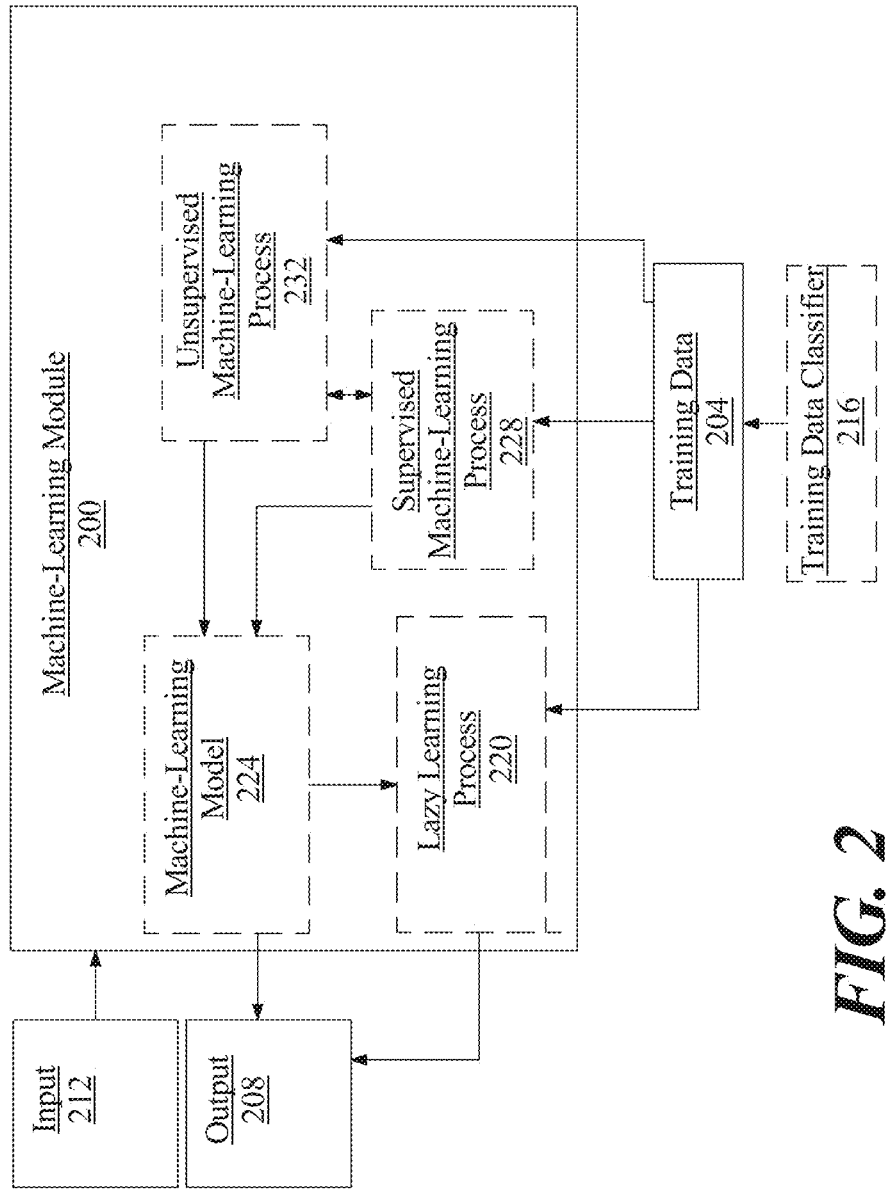
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example inputs may include longevity measurement, and outputs may include target longevity factor. As another non-limiting example, inputs may include longevity treatment and corresponding longevity measurements, and outputs may include longevity treatment protocol.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to the target longevity factor, and the longevity treatment protocol.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively, or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs as described above in this disclosure as inputs, outputs as described above in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 3:
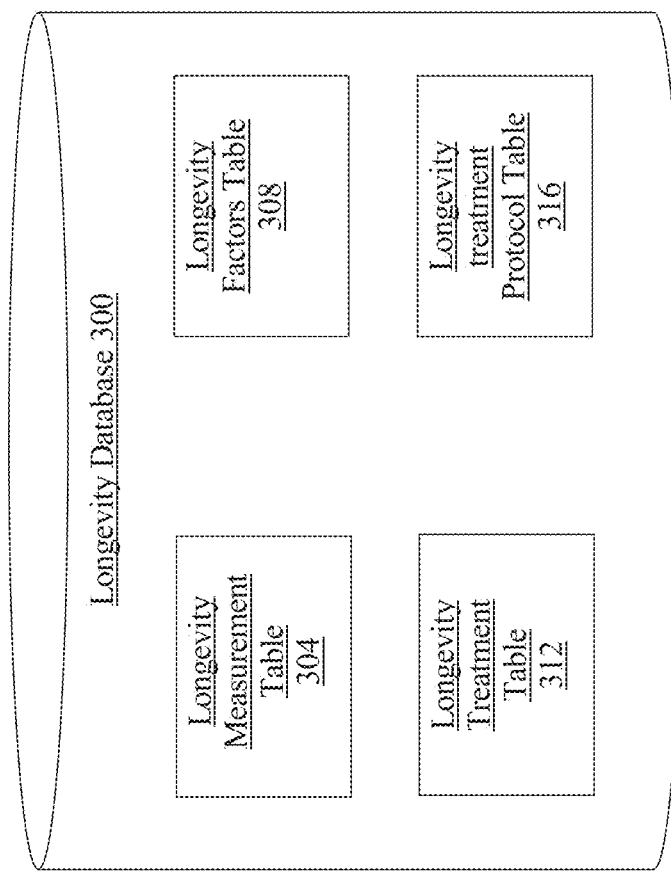
FIG. 3 is a block diagram of an exemplary embodiment of a longevity database.

Referring now to FIG. 3, a non-limiting exemplary embodiment of a longevity database 300 is illustrated. Processor 104 may be communicatively connected with longevity database 300. For example, in some cases, database 300 may be local to processor 104. Alternatively, or additionally, in some cases, database 300 may be remote to processor 104 and communicative with processor 104 by way of one or more networks. Network may include, but not limited to, a cloud network, a mesh network, or the like. By way of example, a "cloud-based" system, as that term is used herein, can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connect directly, dynamically, and non-hierarchically to as many other computing devices as possible. A "network topology" as used in this disclosure is an arrangement of elements of a communication network. Database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 3, at least the processor 104 may, alternatively or additionally, store and/or retrieve data from a longevity measurement table 304, longevity factor table 308, longevity treatment table 312, and longevity treatment protocol table 316. Determinations by a machine learning process may also be stored and/or retrieved from the nutrition database 300, for instance in non-limiting examples a misreporting factor. As a non-limiting example, longevity database 300 may organize data according to one or more longevity database 300 tables. One or more database tables may be linked to one another by, for instance in a non-limiting example, common column values. For instance, a common column between two tables of database may include an identifier of a submission, such as a form entry, textual submission, research paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which data from one or more tables may be linked and/or related to data in one or more other tables.

Still referring to FIG. 3, in a non-limiting embodiment, one or more longevity database tables of a database may include, but is not limited to, a longevity measurement table 304, which may include longevity measurement for use in identifying longevity measurement of a user and/or correlating longevity marker data, entries indicating values and/or degrees of relevance to and/or efficacy in identifying longevity measurement pertaining to a user, and/or other elements of data processor 104 and/or system 100 may use to determine values and/or usefulness and/or relevance of longevity marker data in identifying longevity measurements as described in this disclosure. One or more tables may include a longevity measurement table 304, which may correlate longevity markers and/or combinations thereof to one or more longevity measurements; longevity measurement table 304 may contain a plurality of entries associating at least an element of longevity marker with longevity measurement. One or more tables may include, without limitation, a longevity factor table 308, which may contain one or more inputs identifying one or more categories of data, for instance demographic data, medical history data, physiological data, or the like. One or more tables may include a longevity factor table 308, which may contain one or more entries indicating longevity factors pertaining to the user, entries indicating values and/or degrees of relevance to and/or efficacy in identifying target longevity factor pertaining to a user, and/or other elements of data processor 104 and/or system 100 may use to determine values and/or usefulness and/or relevance of the corresponding evaluation score of the longevity factor as described in this disclosure. One or more tables may include a longevity factor table 308, which may correlate evaluation score and/or combinations thereof to one or more longevity factors; longevity factor table 308 may contain a plurality of entries associating at least an element of evaluation score with longevity factor. One or more tables may include, without limitation, a longevity treatment table 312, which may include one or more entries describing detailed instructions, or prescriptions that may include remediation corresponding to one or more longevity factors. One or more tables may include, without limitation, a longevity treatment protocol tale 316, which may include one or more entries indicating the longevity treatment corresponding to one or more longevity factors.

Figure 4:
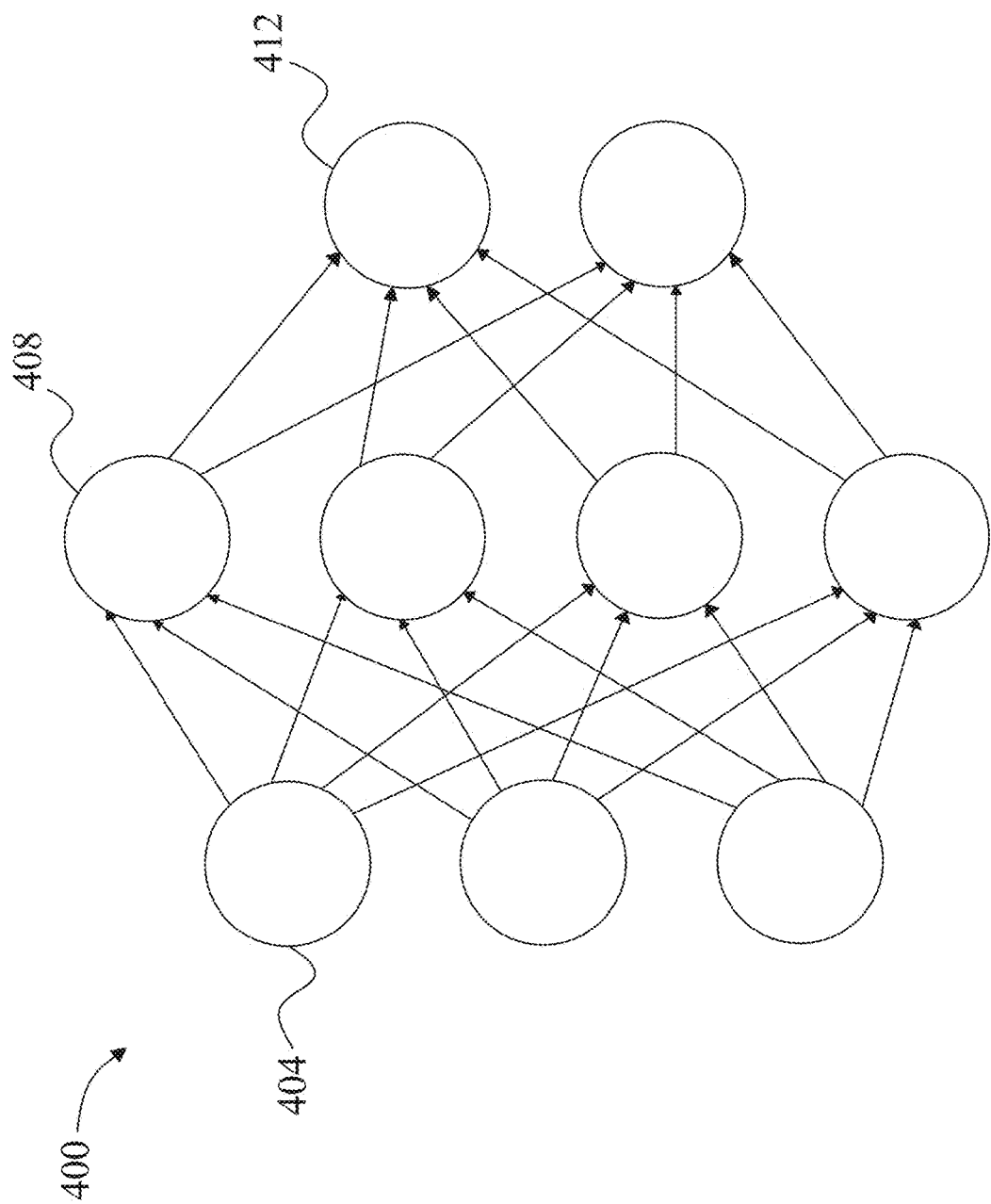
FIG. 4 is a diagram of an exemplary embodiment of neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
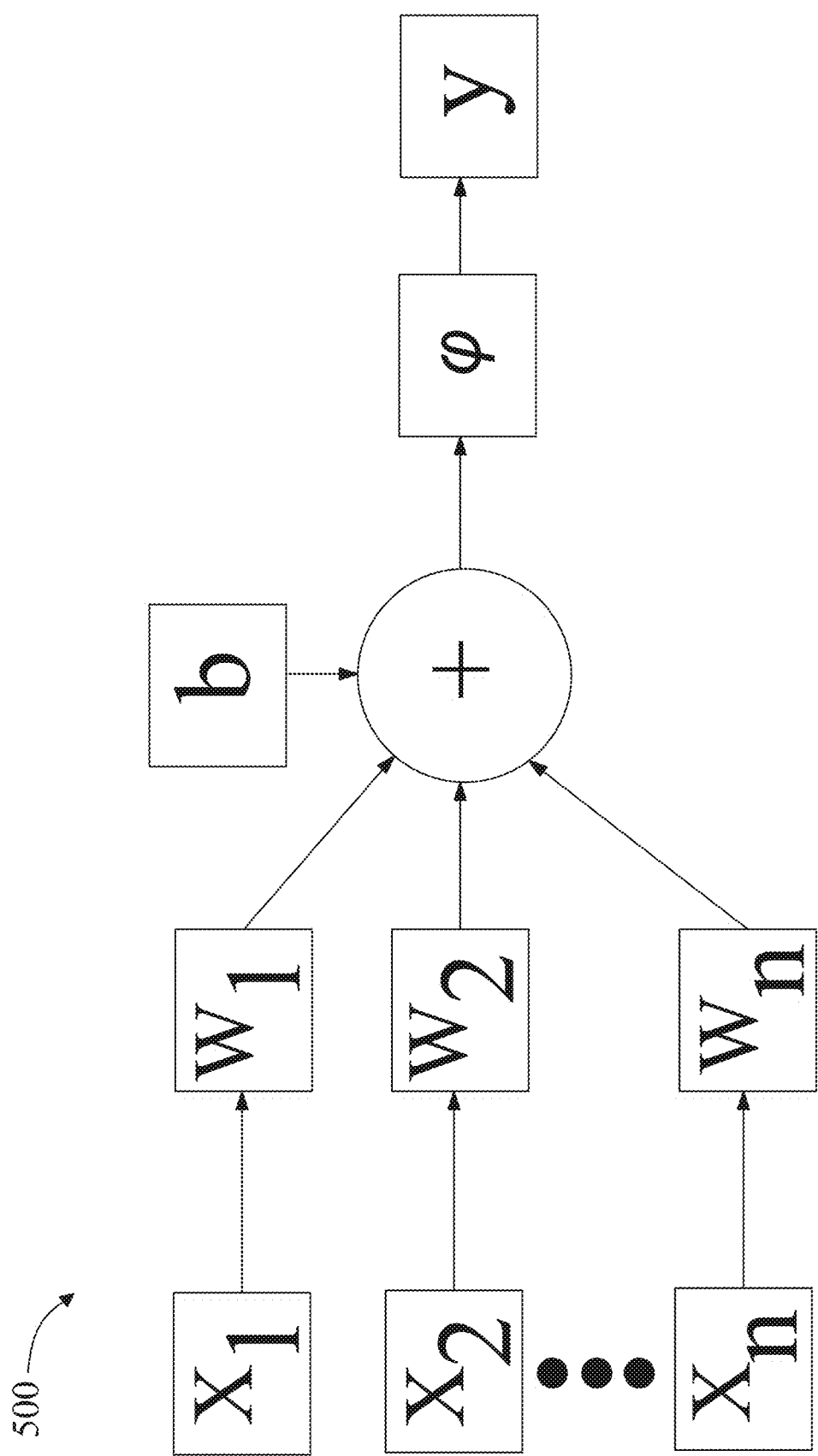
FIG. 5 is a diagram of an exemplary embodiment of a node of a neural network.

Referring now to FIG. 5, an exemplary embodiment of a node of a neural network is illustrated. A node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally, or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights wi may be determined by training a neural network using training data, which may be performed using any suitable process as described above.

Figure 6:
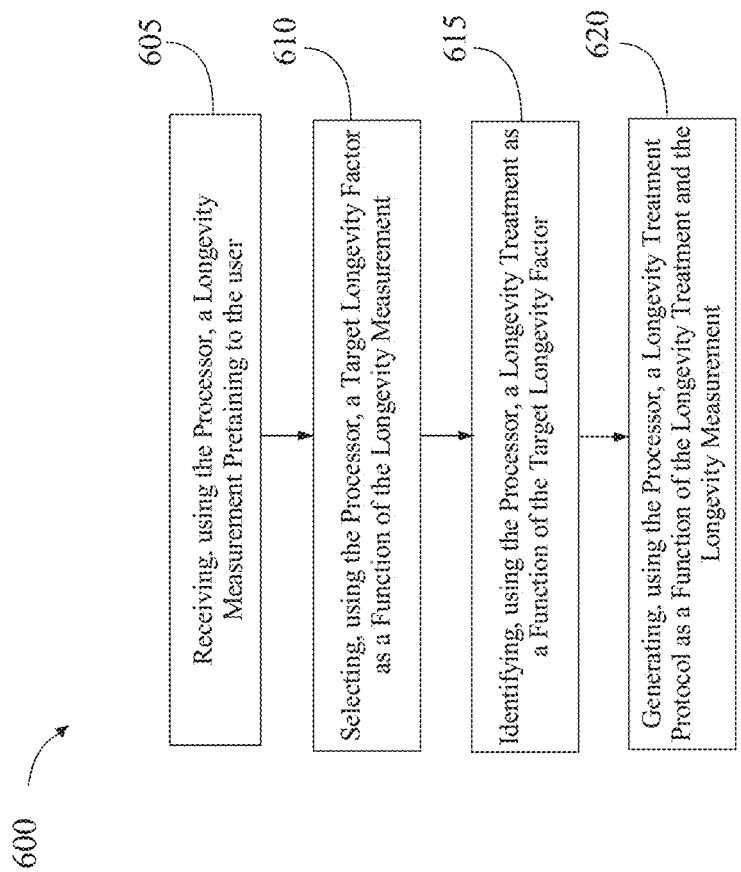
FIG. 6 is a flow diagram of an exemplary method of extending longevity.

Referring now to FIG. 6, an exemplary method 600 for extending longevity is illustrated. Method 600 includes a step 605, of receiving, using a processor, a longevity measurement pertaining to a user, without limitation, as described above in reference to FIGS. 1-5. In some embodiments, the longevity measurement may include a longevity marker associated with the user. Longevity marker associated with user are described further with respect to FIG. 1. In some embodiments, step 605 of receiving the longevity measurement may include selecting a baseline longevity assessment for the user and receiving the longevity measurement pertaining to the user as a function of the baseline longevity assessment result. The baseline longevity assessment is described further with respect to FIG. 1. In some embodiments, the longevity measurement may be stored in the longevity database. This may be implemented, without limitation, as described above with reference to FIGS. 1-5. As an example, longevity database may be consistent with longevity database 300 described with reference to FIG. 3.

With continued reference to FIG. 6, method 600 includes a step 610 of selecting, using the processor, a target longevity factor as a function of the longevity measurement. This may be implemented, without limitation, as described above with reference to FIGS. 1-5. In some embodiments, the longevity factor may include an evaluation score. In some embodiments, the longevity factor may identify one or more disbalanced health area of the user. In some embodiments, step 610 of selecting the target longevity factor may include using a machine-learning process trained with longevity factor training data, wherein the longevity factor training data contains a plurality of inputs containing longevity measurements correlated to a plurality of outputs containing target longevity factors. This may be implemented, without limitation, as described above with reference to FIGS. 1-5. In some embodiments, the longevity training data may include selection of prior longevity measurement 304 and/or prior longevity factor 308 of longevity database 300. This may be implemented, without limitation, as described above with reference to FIGS. 1-5.

With continued reference to FIG. 6, method 600 includes a step 615 of identifying, using the processor, a longevity treatment as a function of the target longevity factor. This may be implemented, without limitation, as described above with reference to FIGS. 1-5. In some embodiments, the longevity treatment may include a set of consumable longevity-extending ingredients. In some embodiments, the longevity treatment may also include a set of executable longevity-extending procedures. In some embodiments, the longevity treatment may include a lifestyle factor. This may be implemented, without limitation, as described above with reference to FIGS. 1-5.

With continued reference to FIG. 6, method 600 includes a step 620 of generating, using the processor, a longevity treatment protocol as a function of the longevity treatment and the longevity measurements. This may be implemented, without limitation, as described above with reference to FIGS. 1-5. The longevity treatment protocol may include one or more longevity treatments corresponding to one or more longevity factors. =In some embodiments, step 620 of generating the longevity treatment protocol may include using a machine-learning process trained with longevity treatment training data, wherein the longevity treatment training data contains a plurality of inputs containing longevity treatments and corresponding longevity measurements correlated to a plurality of outputs containing longevity treatment protocol. In some embodiments, generating the longevity treatment protocol may include updating the longevity treatment protocol as a function of one or more post longevity measurements in addition to longevity measurement and the trained machine-learning process. This may be implemented, without limitation, as described above with reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
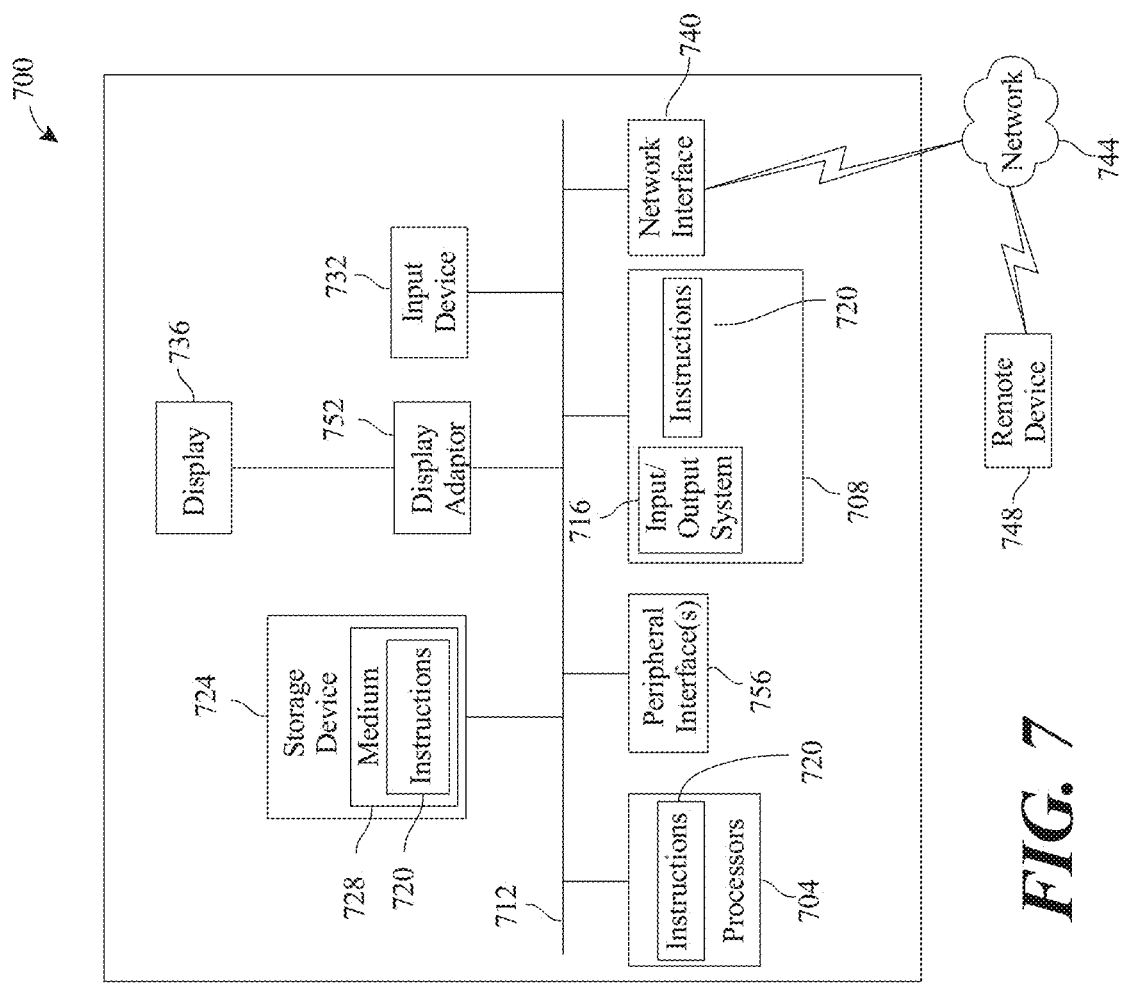
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for extending longevity, wherein the apparatus comprises:
   at least a processor; and
   a memory communicatively connected to the at least a processor, the memory containing instructions configuring the at least a processor to:
   receive a longevity measurement pertaining to a user wherein the longevity measurement further comprises at least a biomarker;
   select a target longevity factor as a function of the longevity measurement, wherein selecting the target longevity factor further comprises:
      training a machine-learning model using longevity factor training data, wherein the longevity factor training data comprises at least a longevity measurement input correlated to at least a target longevity factor output;
      generating, using the trained machine-learning model, the target longevity factor based on the longevity measurement; and
      retraining the machine-learning model with the updated longevity factor training data;
   identify a longevity treatment as a function of the target longevity factor and the trained machine-learning model; and
   generate a longevity treatment protocol pertaining to the user as a function of the longevity treatment and the longevity measurement, wherein the longevity treatment protocol comprises a detailed plan of medical treatment, and wherein generating the longevity treatment protocol comprises:
      receiving one or more post longevity measurements, wherein the one or more post longevity measurements is received at a time interval after the longevity measurement; and
      updating the longevity treatment protocol as a function of the one or more post longevity measurements, wherein updating the longevity treatment protocol comprises removing a longevity factor from the longevity treatment protocol in response to receiving the one or more post longevity measurements.

2. The apparatus of claim 1, wherein receiving the longevity measurement further comprises:
   selecting a baseline longevity assessment for the user; and
   receiving the longevity measurement pertaining to the user as a function of the baseline longevity assessment.

3. The apparatus of claim 1, wherein selecting the baseline longevity assessment further comprises an initial baseline longevity assessment and periodic repetition of the baseline longevity assessment.

4. The apparatus of claim 1, wherein the target longevity factor identifies a disbalanced health area of the user.

5. The apparatus of claim 1, wherein the longevity treatment comprises a set of consumable longevity-extending ingredients.

6. The apparatus of claim 1, wherein the longevity treatment comprises a lifestyle factor pertaining to the user.

7. The apparatus of claim 1, wherein generating the longevity treatment protocol further comprises:
   training an additional machine-learning process using longevity treatment training data, wherein the longevity treatment training data comprises a plurality of inputs comprising longevity treatments and corresponding longevity measurements correlated to a plurality of outputs comprising longevity treatment protocols; and
   generating the longevity treatment protocol pertaining to the user as a function of the trained machine-learning process.

8. The apparatus of claim 1, wherein the longevity measurement comprises a timestamp.

9. The apparatus of claim 1, wherein the baseline longevity assessment comprises a set of actions performed by the user.

10. The method of claim 1, wherein the baseline longevity assessment comprises a set of actions performed by the user.

11. A method for extending longevity, wherein the method comprises:
receiving, using a processor, a longevity measurement pertaining to a user, wherein the longevity measurement further comprises at least a biomarker;
selecting, using the processor, a target longevity factor as a function of the longevity measurement wherein selecting the target longevity factor further comprises:
training a machine-learning model using longevity factor training data, wherein the longevity factor training data comprises at least a longevity measurement input correlated to at least a target longevity factor output;
generating, using the trained machine-learning model, the target longevity factor based on the longevity measurement; and
retraining the machine-learning model with the updated longevity factor training data;
identifying, using the processor, a longevity treatment as a function of the target longevity factor and the machine-learning model; and
generating, using the processor, a longevity treatment protocol pertaining to the user as a function of the longevity treatment and the longevity measurement, wherein the longevity treatment protocol comprises a detailed plan of medical treatment, and wherein generating the longevity treatment protocol comprises:
receiving one or more post longevity measurements, wherein the one or more post longevity measurements is received at a time interval after the longevity measurement; and
updating the longevity treatment protocol as a function of the one or more post longevity measurements, wherein updating the longevity treatment protocol comprises removing a longevity factor from the longevity treatment protocol in response to receiving the one or more post longevity measurements.

12. The method of claim 11, wherein receiving the longevity measurement further comprises:
selecting a baseline longevity assessment for the user; and
receiving the longevity measurement pertaining to the user as a function of the baseline longevity assessment result.

13. The method of claim 11, wherein selecting the baseline longevity assessment comprises an initial baseline longevity assessment and periodic repetition of the initial baseline longevity assessment.

14. The method of claim 11, wherein the target longevity factor identifies a disbalanced health area of the user.

15. The method of claim 11, wherein the longevity treatment comprises a set of consumable longevity-extending ingredients.

16. The method of claim 11, wherein the longevity treatment comprises a lifestyle factor pertaining to the user.

17. The method of claim 11, wherein generating the longevity treatment protocol further comprises:
training an additional machine-learning process using longevity treatment training data, wherein the longevity treatment training data comprises a plurality of inputs comprising longevity treatments and corresponding longevity measurements correlated to a plurality of outputs comprising longevity treatment protocols; and
generating the longevity treatment protocol pertaining to the user as a function of the trained machine-learning process.

18. The method of claim 11, wherein the longevity measurement comprises a timestamp.

* * * * *